(12) United States Patent
Grace et al.

(10) Patent No.: US 11,497,906 B2
(45) Date of Patent: Nov. 15, 2022

(54) IMPLANTABLE BLOOD PUMP ASSEMBLY INCLUDING OUTFLOW GRAFT FIXATION CLIP

(71) Applicant: TC1 LLC, St. Paul, MN (US)

(72) Inventors: Christopher Grace, Wilmington, MA (US); Dustin S. West, Leominster, MA (US); Matthew Wagers, Cambridge, MA (US)

(73) Assignee: TC1 LLC, St. Paul, MN (US)

( * ) Notice: Subject to any disclaimer, the term of this patent is extended or adjusted under 35 U.S.C. 154(b) by 415 days.

(21) Appl. No.: 16/597,084

(22) Filed: Oct. 9, 2019

(65) Prior Publication Data

US 2020/0121836 A1  Apr. 23, 2020

Related U.S. Application Data

(60) Provisional application No. 62/747,884, filed on Oct. 19, 2018.

(51) Int. Cl.
*A61M 60/859* (2021.01)
*A61B 17/34* (2006.01)
(Continued)

(52) U.S. Cl.
CPC ....... *A61M 60/859* (2021.01); *A61B 17/3421* (2013.01); *A61M 60/148* (2021.01);
(Continued)

(58) Field of Classification Search
CPC .. A61M 60/50; A61M 60/148; A61M 60/857; A61M 60/205; A61M 60/859; A61B 17/3421; A61B 2017/3425
See application file for complete search history.

(56) References Cited

U.S. PATENT DOCUMENTS 9,849,224 B2   12/2017  Angwin et al.
2012/0226096 A1*  9/2012  Callaway ............ A61M 60/135
                                                600/16
(Continued)

OTHER PUBLICATIONS

Popatov et al., "Strategy for surgical correction and mitigation of outflow graft twist with a centrifugal-flow left ventricular assist system," The Journal of Heart and Lung Transplantation, vol. 37, No. 5, May 2018, pp. 670-673.
(Continued)

*Primary Examiner* — Lindsey G Wehrheim
(74) *Attorney, Agent, or Firm* — Armstrong Teasdale LLP

(57) ABSTRACT

Disclosed herein is an outflow graft assembly for an implantable blood pump. The outflow graft assembly includes a graft, a locking nut including a plurality of planar edges and a plurality of corners, and a U-shaped fixation clip. The U-shaped fixation clip includes a first flat segment including a first flexure including a first locking feature, a second flat segment including a second flexure including a second locking feature, an arcuate segment extending between the first flat segment and the second flat segment, and a lip including a first flat and a second flat. The U-shaped fixation clip is configured to engage the locking nut such that the first and second locking features contact associated corners of the plurality of corners and the first and second flats contact associated planar edges of the plurality of planar edges, thereby preventing rotation of the locking nut relative to the fixation clip.

20 Claims, 8 Drawing Sheets

(51) Int. Cl.
*A61M 60/857* (2021.01)
*A61M 60/50* (2021.01)
*A61M 60/148* (2021.01)
*A61M 60/205* (2021.01)

(52) U.S. Cl.
CPC .......... *A61M 60/205* (2021.01); *A61M 60/50* (2021.01); *A61M 60/857* (2021.01); *A61B 2017/3425* (2013.01)

(56) References Cited

U.S. PATENT DOCUMENTS

2013/0225909 A1* 8/2013 Dormanen ......... A61M 39/1011
600/16
2013/0261375 A1 10/2013 Callaway et al.

OTHER PUBLICATIONS

International Search Report and Written Opinion for International Patent Application No. PCT/US2019/055357, dated Dec. 19, 2019, 14 pages.

* cited by examiner

IMPLANTABLE BLOOD PUMP ASSEMBLY INCLUDING OUTFLOW GRAFT FIXATION CLIP

CROSS REFERENCE TO RELATED APPLICATIONS

This application claims priority to provisional application Ser. No. 62/747,884, filed Oct. 19, 2018, which is incorporated herein in its entirety.

BACKGROUND OF THE DISCLOSURE a. Field of the Disclosure

The present disclosure relates generally to mechanical circulatory support systems, and more specifically relates to implantable blood pump assemblies that include a fixation clip in an outflow assembly.

b. Background

Ventricular assist devices, known as VADs, are implantable blood pumps used for both short-term (i.e., days, months) and long-term (i.e., years or a lifetime) applications where a patient's heart is incapable of providing adequate circulation, commonly referred to as heart failure or congestive heart failure. A patient suffering from heart failure may use a VAD while awaiting a heart transplant or as a long term destination therapy. In another example, a patient may use a VAD while recovering from heart surgery. Thus, a VAD can supplement a weak heart (i.e., partial support) or can effectively replace the natural heart's function. VADs can be implanted in the patient's body and powered by an electrical power source inside or outside the patient's body.

A controller can be used to control operation of the implanted VAD. The controller can be operatively connected to the VAD via a wired and/or mechanical connection, which can be used to supply the VAD with operating power (e.g., electrical and/or mechanical power) and control signals to control the operation of the VAD.

At least some VADs include an outflow assembly that connects a pump assembly to a graft of an outflow cannula.

SUMMARY OF THE DISCLOSURE

The present disclosure is directed to an outflow graft assembly for an implantable blood pump. The outflow graft assembly includes a graft, a locking nut coupled to the graft, the locking nut including a plurality of planar edges and a plurality of corners, each corner extending between a pair of the plurality of planar edges, and a U-shaped fixation clip. The U-shaped fixation clip includes a first flat segment including a first flexure defined by a pair of slits formed in the first flat segment, the first flexure including a first locking feature, a second flat segment including a second flexure defined by a pair of slits formed in the second flat segment, the second flexure including a second locking feature, an arcuate segment extending between the first flat segment and the second flat segment, and a lip including a first flat on the first segment and a second flat on the second segment. The U-shaped fixation clip is configured to engage the locking nut such that the first and second locking features contact associated corners of the plurality of corners and the first and second flats contact associated planar edges of the plurality of planar edges, thereby preventing rotation of the locking nut relative to the fixation clip.

The present disclosure is further directed to a fixation clip for an outflow graft assembly of an implantable blood pump. The fixation clip includes a first flat segment including a first flexure defined by a pair of slits formed in the first flat segment, the first flexure including a first locking feature, a second flat segment including a second flexure defined by a pair of slits formed in the second flat segment, the second flexure including a second locking feature, an arcuate segment extending between the first flat segment and the second flat segment, and a lip including a first flat on the first segment and a second flat on the second segment. The fixation clip is configured to engage a locking nut such that the first and second locking features contact associated corners of a plurality of corners of the locking nut and the first and second flats contact associated planar edges of a plurality of planar edges of the locking nut, thereby preventing rotation of the locking nut relative to the fixation clip.

DETAILED DESCRIPTION OF THE DISCLOSURE

The present disclosure is directed to an outflow graft assembly of an implantable blood pump assembly. The outflow graft assembly includes a graft, a locking nut coupled to the graft, the locking nut including a plurality of planar edges and a plurality of corners, each corner extending between a pair of the plurality of planar edges, and a U-shaped fixation clip. The U-shaped fixation clip includes a first flat segment including a first flexure defined by a pair of slits formed in the first flat segment, the first flexure including a first locking feature, a second flat segment including a second flexure defined by a pair of slits formed in the second flat segment, the second flexure including a second locking feature, an arcuate segment extending between the first flat segment and the second flat segment, and a lip including a first flat on the first segment and a second flat on the second segment. The U-shaped fixation clip is configured to engage the locking nut such that the first and second locking features contact associated corners of the plurality of corners and the first and second flats contact associated planar edges of the plurality of planar edges, thereby preventing rotation of the locking nut relative to the fixation clip.

Figure 1:
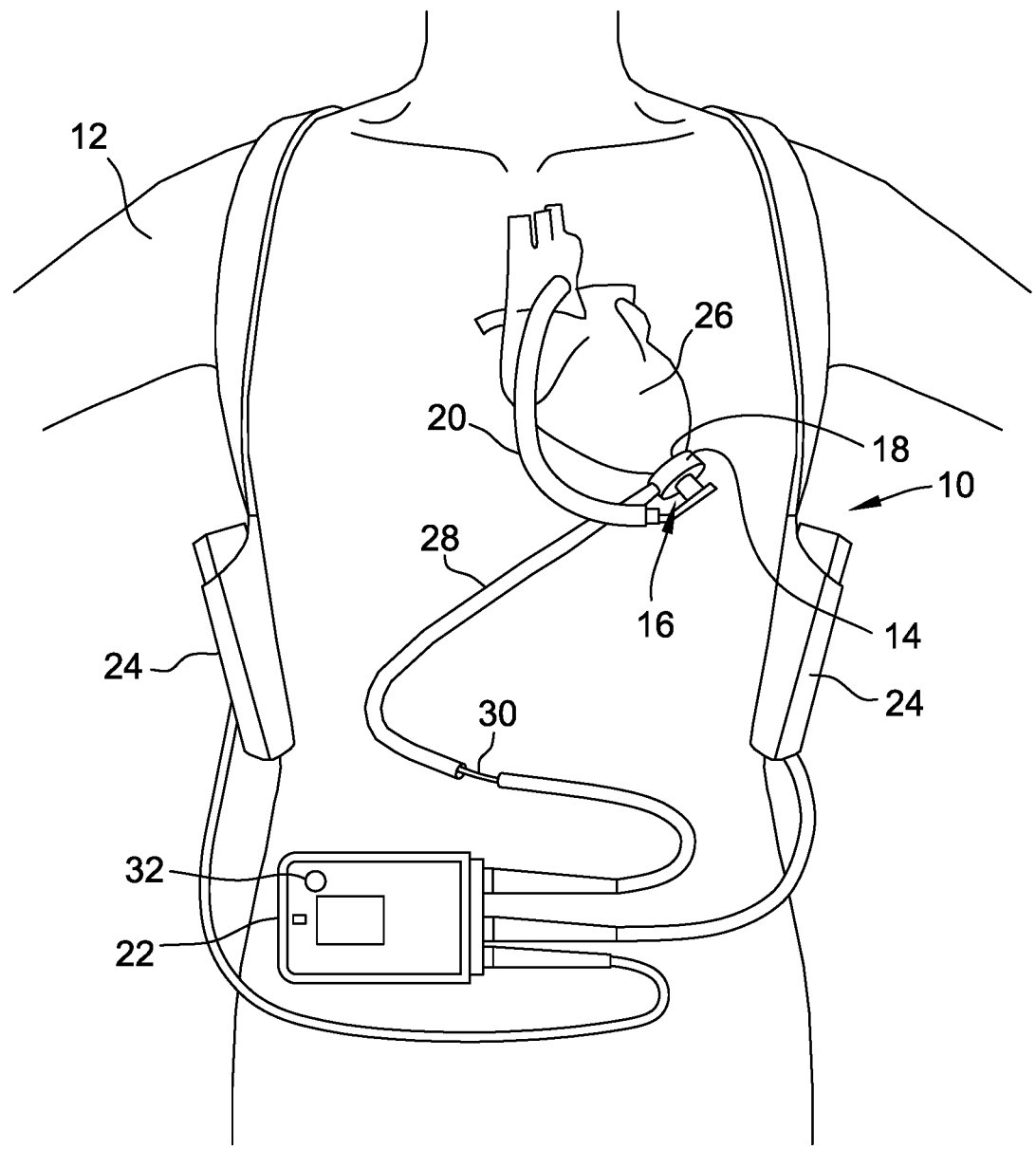
FIG. 1 is an illustration of a mechanical circulatory support system implanted in a patient's body.

Referring now to the drawings, FIG. 1 is an illustration of a mechanical circulatory support system 10 implanted in a patient's body 12. The mechanical circulatory support system 10 includes an implantable blood pump assembly 14 that includes a blood pump 16, a ventricular cuff 18, and an outflow cannula 20. The mechanical circulatory support system 10 also includes an external system controller 22 and one or more power sources 24.

The blood pump assembly 14 can be implemented as a ventricular assist device (VAD) or can include a VAD that is attached to an apex of the left ventricle, as illustrated, or the right ventricle, or both ventricles of the heart 26. The blood pump assembly 14 can be attached to the heart 26 via the ventricular cuff 18 which is sewn to the heart 26 and coupled to the blood pump assembly 14. The other end of the blood pump assembly 14 connects to the ascending or descending aorta via the outflow cannula 20 so that the blood pump assembly 14 effectively diverts blood from the weakened ventricle and propels it to the aorta for circulation to the rest of the patient's vascular system. The VAD can include a centrifugal (as shown) or axial flow pump as described in further detail herein that is capable of pumping the entire output delivered to the left ventricle from the pulmonary circulation (i.e., up to 10 liters per minute).

FIG. 1 illustrates the mechanical circulatory support system 10 during battery powered operation. A driveline 28 that exits through the patient's abdomen 30 connects the implanted blood pump assembly 14 to the external system controller 22, which monitors system 10 operation. The system can be powered by either one, two, or more batteries 24. It will be appreciated that although the system controller 22 and power source 24 are illustrated outside/external to the patient body, the driveline 28, system controller 22 and/or power source 24 can be partially or fully implantable within the patient, as separate components or integrated with the blood pump assembly 14.

Figure 2:
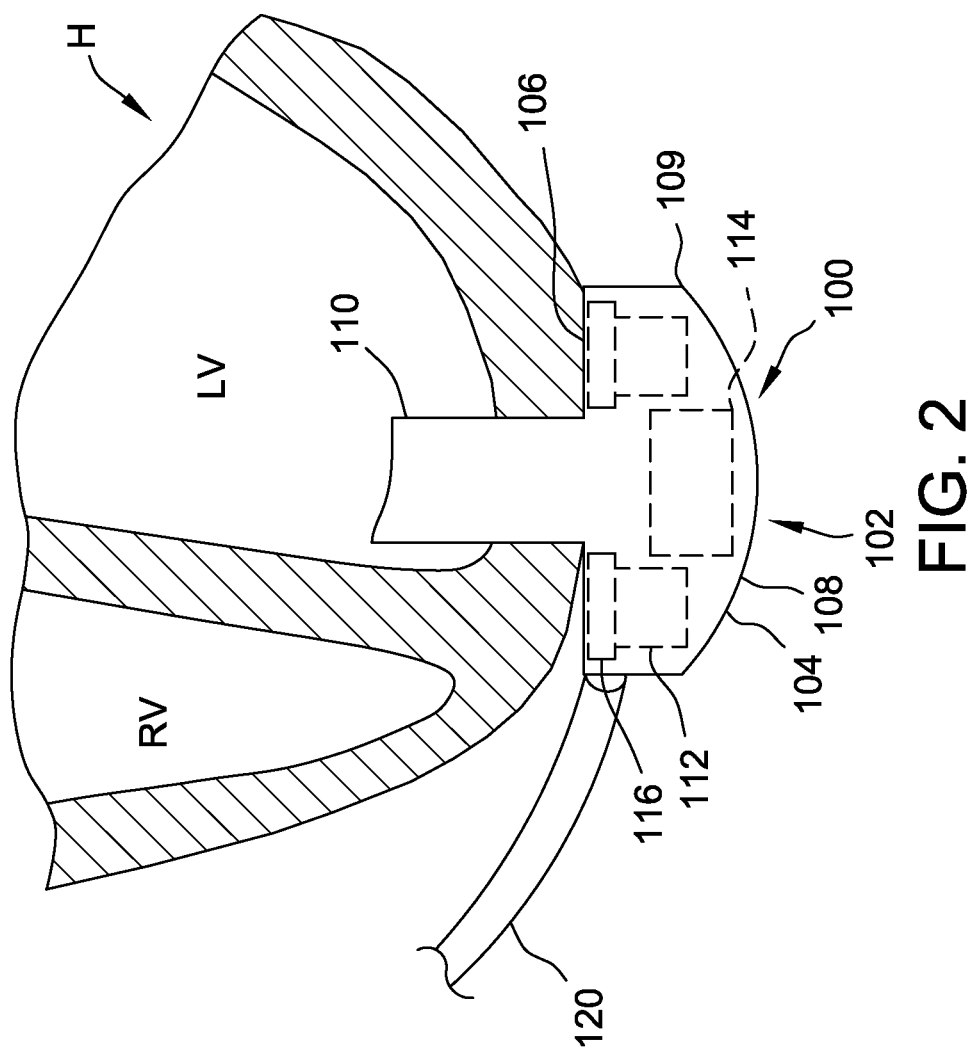
FIG. 2 is an illustration of a blood pump assembly suitable for use in the mechanical circulatory support system of FIG. 1, the blood pump assembly shown in an operational position implanted in a patient's body.
Figure 3:
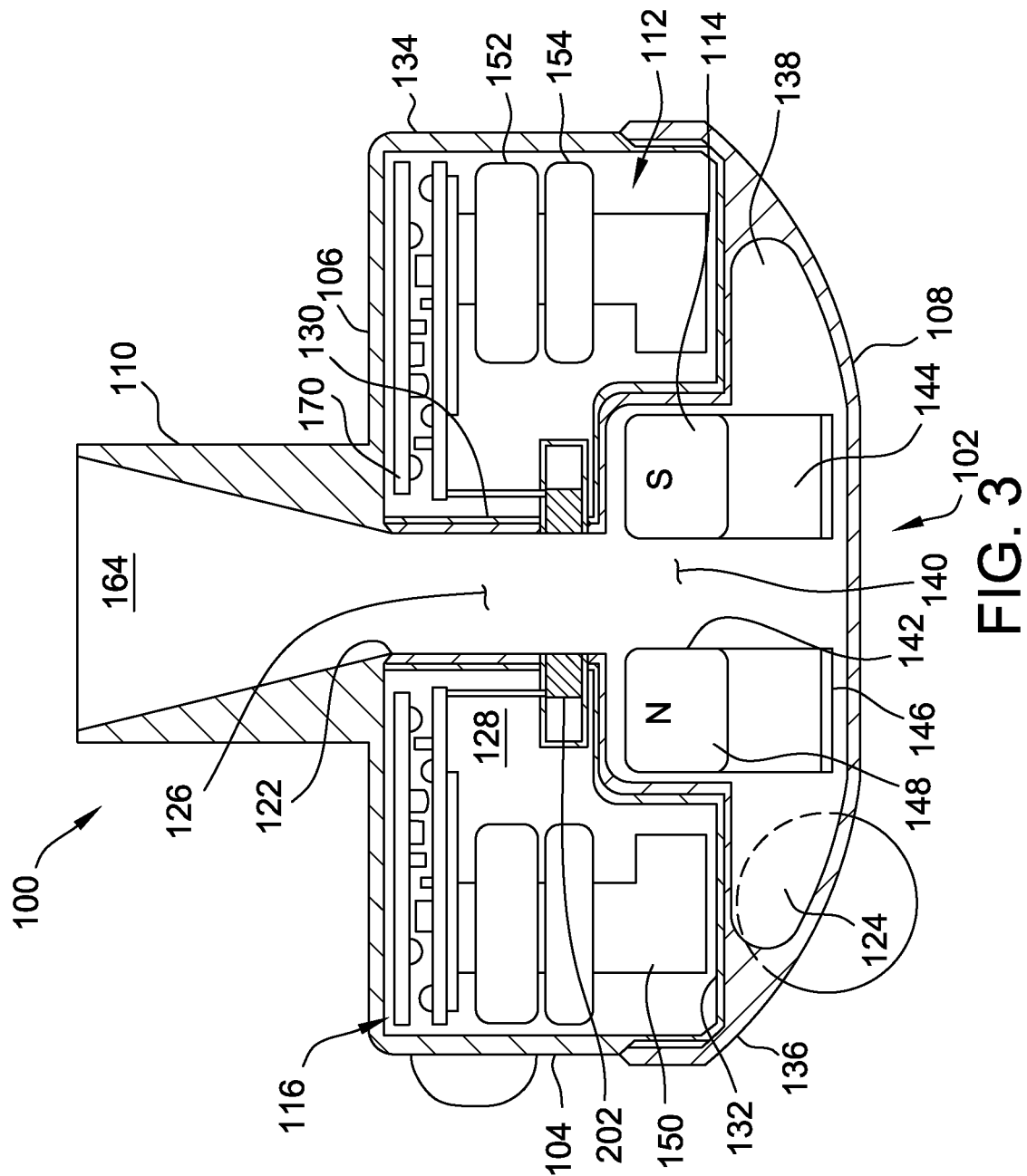
FIG. 3 is a schematic cross-sectional view of the blood pump assembly of FIG. 2.

FIG. 2 is an illustration of an implantable blood pump assembly 100 suitable for use in the mechanical circulatory support system 10 of FIG. 1, where the blood pump assembly 100 is shown in an operational position implanted in a patient's body. FIG. 3 is a schematic cross-sectional view of the blood pump assembly 100 of FIG. 2. In the illustrated embodiment, the blood pump assembly 100 is a left ventricular assist blood pump assembly connected to the left ventricle LV of the heart H.

The blood pump assembly 100 includes a blood pump 102 including a circular shaped housing 104 having a first outer face or wall 106 and a second outer face or wall 108. The blood pump assembly 100 further includes an inlet cannula 110 (generally, an inlet conduit) that, in the illustrated embodiment, extends from the first outer wall 106 of the pump housing 104. When the blood pump assembly 100 is implanted into a patient's body, as shown in FIG. 2, the first outer wall 106 of the housing 104 is positioned against the patient's heart H, and the second outer wall 108 of the housing 104 faces away from the heart H. The inlet cannula 110 extends into the left ventricle LV of the heart H to connect the blood pump assembly 100 to the heart H. The second outer wall 108 of the housing 104 has a chamfered edge 109 to avoid irritating other tissue that may come into contact with the blood pump assembly 100, such as the patient's diaphragm.

The blood pump assembly 100 further includes a stator 112, a rotor 114, an on-board controller 116, and a pressure sensor assembly 118 (FIG. 3), all of which are enclosed within the pump housing 104. In the illustrated embodiment, the stator 112 and the on-board controller 116 are positioned on the inflow side of the pump housing 104 toward the first outer wall 106, and the rotor 114 is positioned along the second outer wall 108. In other embodiments, the stator 112, the rotor 114, and the on-board controller 116 may be positioned at any suitable location within the pump housing 104 that enables the blood pump assembly 100 to function as described herein. Power is supplied to operational components of the blood pump assembly 100 (e.g., the stator 112 and the on-board controller 116) from a remote power supply via a power supply cable 120.

With additional reference to FIG. 3, the pump housing 104 defines an inlet 122 for receiving blood from a ventricle of a heart (e.g., left ventricle LV), an outlet 124 for returning blood to a circulatory system, and a flow path 126 extending from the inlet 122 to the outlet 124. The pump housing 104 further defines an internal compartment 128 separated from the flow path 126, for example, by one or more dividing walls 130.

The pump housing 104 also includes an intermediate wall 132 located between the first outer wall 106 and the second outer wall 108, and a peripheral wall 134 that extends between the first outer wall 106 and the intermediate wall 132. Together, the first outer wall 106, the dividing wall 130, the intermediate wall 132, and the peripheral wall 134 define the internal compartment 128 in which the stator 112 and the on-board controller 116 are enclosed.

In the illustrated embodiment, the pump housing 104 also includes a cap 136 removably attached to the pump housing 104 along the intermediate wall 132. The removable cap 136 includes the second outer wall 108, the chamfered edge 109, and defines the outlet 124. The cap 136 also defines a volute 138 that is in fluid communication with the outlet 124, and a rotor chamber 140 in which the rotor 114 is positioned. The cap 136 can be attached to the pump housing 104 using any suitable connection structure. For example, the cap 136 can be engaged via threads with the peripheral wall 134 to seal the cap 136 in engagement with the peripheral wall 134.

The rotor 114 is positioned within the blood flow path 126, specifically, within the rotor chamber 140, and is operable to rotate in response to an electromagnetic field generated by the stator 112 to pump blood from the inlet 122 to the outlet 124. The rotor defines a central aperture 142 through which blood flows during operation of the blood pump 102. The rotor 114 includes impeller blades 144 located within the volute 138 of the blood flow path 126, and a shroud 146 that covers the ends of the impeller blades 144 facing the second outer wall 108 to assist in directing blood flow into the volute 138.

In the illustrated embodiment, the rotor 114 includes a permanent magnet 148 that defines the central aperture 142. The permanent magnet 148 has a permanent magnetic north pole N and a permanent magnetic south pole S for combined active and passive magnetic levitation of the rotor 114 and for rotation of the rotor 114. In operation, the stator 112 is controlled to drive (i.e., rotate) the rotor and to radially levitate the rotor 114 by generating electromagnetic fields that interact with the permanent magnetic poles S and N of the permanent magnet 148.

Any suitable stator 112 can be employed to rotate the rotor 114. The stator 112 generally includes a plurality of winding structures that generate suitable electromagnetic fields that interact with the rotor 114 to cause rotor 114 to rotate and levitate. In the illustrated embodiment, the stator 112 includes a plurality of pole pieces 150 arranged circumferentially at intervals around the dividing wall 130. The example blood pump assembly 100 includes six pole pieces 150, two of which are visible in FIG. 3. In other embodiments, the blood pump assembly 100 can include more than or less than six pole pieces, such as four pole pieces, eight pole pieces, or any other suitable number of pole pieces that enables the blood pump assembly 100 to function as described herein. In the illustrated embodiment, each of the pole pieces 150 includes a drive coil 152 for generating an electromagnetic field to rotate the rotor 114, and a levitation coil 154 for generating an electromagnetic field to control the radial position of the rotor 114.

Each of the drive coils 152 and the levitation coils 154 includes multiple windings of a conductor wound around the pole pieces 150. The drive coils 152 and the levitation coils 154 of the stator 112 are arranged in opposing pairs and are controlled to drive the rotor and to radially levitate the rotor 114 by generating electromagnetic fields that interact with the permanent magnetic poles S and N of the permanent magnet 148. Suitable methods for generating electromagnetic fields to rotate and radially levitate the rotor 114 are described, for example, in U.S. Pat. No. 9,849,224, the entire contents of which are incorporated herein by reference for all purposes. Although the drive coil 152 and levitation coil 154 are shown as separate coils in the illustrated embodiment, it should be understood that the drive coil 152 and levitation coil 154 may be implemented as a single coil configured to generate electromagnetic fields for both rotating and radially levitating the rotor 114.

Figure 4:
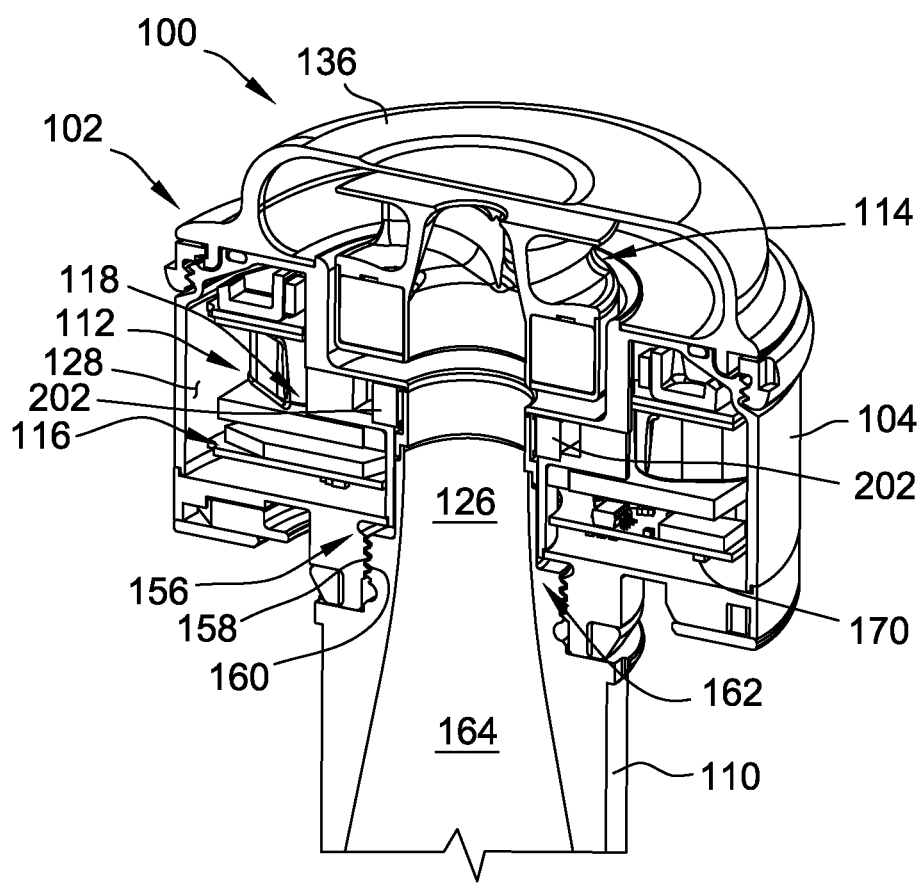
FIG. 4 is a perspective cut away view of the blood pump assembly of FIG. 2.

The inlet cannula 110 is attached to the pump housing 104 at the inlet 122. As shown in FIG. 4, the pump housing 104 includes an inlet cannula receiving portion 156 that includes suitable connecting structure for connecting the inlet cannula 110 to the pump housing 104. In the illustrated embodiment, the pump housing 104 includes an internally threaded sleeve 158 that threadably engages external threads 160 on a downstream end 162 of the inlet cannula 110 to connect the inlet cannula 110 to the pump housing 104.

The inlet cannula 110 defines an inlet flow path 164 that supplies blood to the inlet 122 of the pump housing 104. As shown in FIG. 4, in the illustrated embodiment, the inlet cannula 110 extends into the blood flow path 126 defined by the pump housing 104 such that the inlet flow path 164 partially overlaps with the blood flow path 126.

The downstream end 162 of the inlet cannula 110 has a reduced cross-sectional area (e.g., relative to an upstream end of the inlet cannula 110) that produces a localized region of high velocity blood flow through the inlet flow path 164 and the blood flow path 126. Specifically, the cross-sectional area of the inlet flow path 164 gradually and continuously decreases towards the downstream end 162 of the inlet cannula 110 such that blood flowing through the inlet cannula 110 at a constant flow rate will experience an increase in velocity as it flows through the downstream end 162 of the inlet cannula 110. Consequently, during operation of the blood pump assembly 100, the reduced-cross-sectional area of the downstream end 162 produces a localized region of high velocity blood flow that flows through the inlet 122 and through the blood flow path 126.

In some embodiments, the on-board controller 116 is configured to control the speed of the rotor 114 according to a speed profile that defines a time-variable speed set point of the rotor 114. In such embodiments, the on-board controller 116 can be configured to modulate the speed of the rotor 114 to different speed set points within a single cardiac cycle of a patient's heart. In other embodiments, the on-board controller 116 is configured to control the speed of the rotor 114 according to a fixed (i.e., time invariable) speed set point. In such embodiments, the on-board controller 116 can be configured to control the speed of the rotor 114 to achieve an average speed equal to the speed set point. Rotor speed profiles and/or set points can be established by user input, for example, from a patient or a clinician, and can be stored in a memory device of the on-board controller 116.

The on-board controller 116 can include one or more modules or devices that are enclosed within pump housing 104. The on-board controller 116 can generally include any suitable computer and/or other processing unit, including any suitable combination of computers, processing units and/or the like that may be communicatively coupled to one another (e.g., on-board controller 116 can form all or part of a controller network). Thus, on-board controller 116 can include one or more processor(s) and associated memory device(s) configured to perform a variety of computer-implemented functions (e.g., performing the methods, steps, calculations and/or the like disclosed herein). As used herein, the term "processor" refers not only to integrated circuits referred to in the art as being included in a computer, but also refers to a controller, a microcontroller, a micro-computer, a programmable logic controller (PLC), an application specific integrated circuit (ASIC), a digital signal processor (DSP), a field programmable gate array (FPGA), and other programmable circuits. Additionally, the memory device(s) of on-board controller 116 may generally include memory element(s) including, but not limited to, non-transitory computer readable medium (e.g., random access memory (RAM)), computer readable non-volatile medium (e.g., a flash memory), a floppy disk, a compact disc-read only memory (CD-ROM), a magneto-optical disk (MOD), a digital versatile disc (DVD) and/or other suitable memory elements. Such memory device(s) can generally be configured to store suitable computer-readable instructions that, when implemented by the processor(s), configure the on-board controller 116 to perform various functions including, but not limited to, controlling the supply of electrical current to the stator 112, and various other suitable computer-implemented functions.

In the illustrated embodiment, the on-board controller 116 is implemented as one or more circuit boards 170 and various components carried on the circuit boards (e.g., processors and memory devices) to control operation of the pump 102 by controlling the electrical supply to the stator 112.

Figure 5:
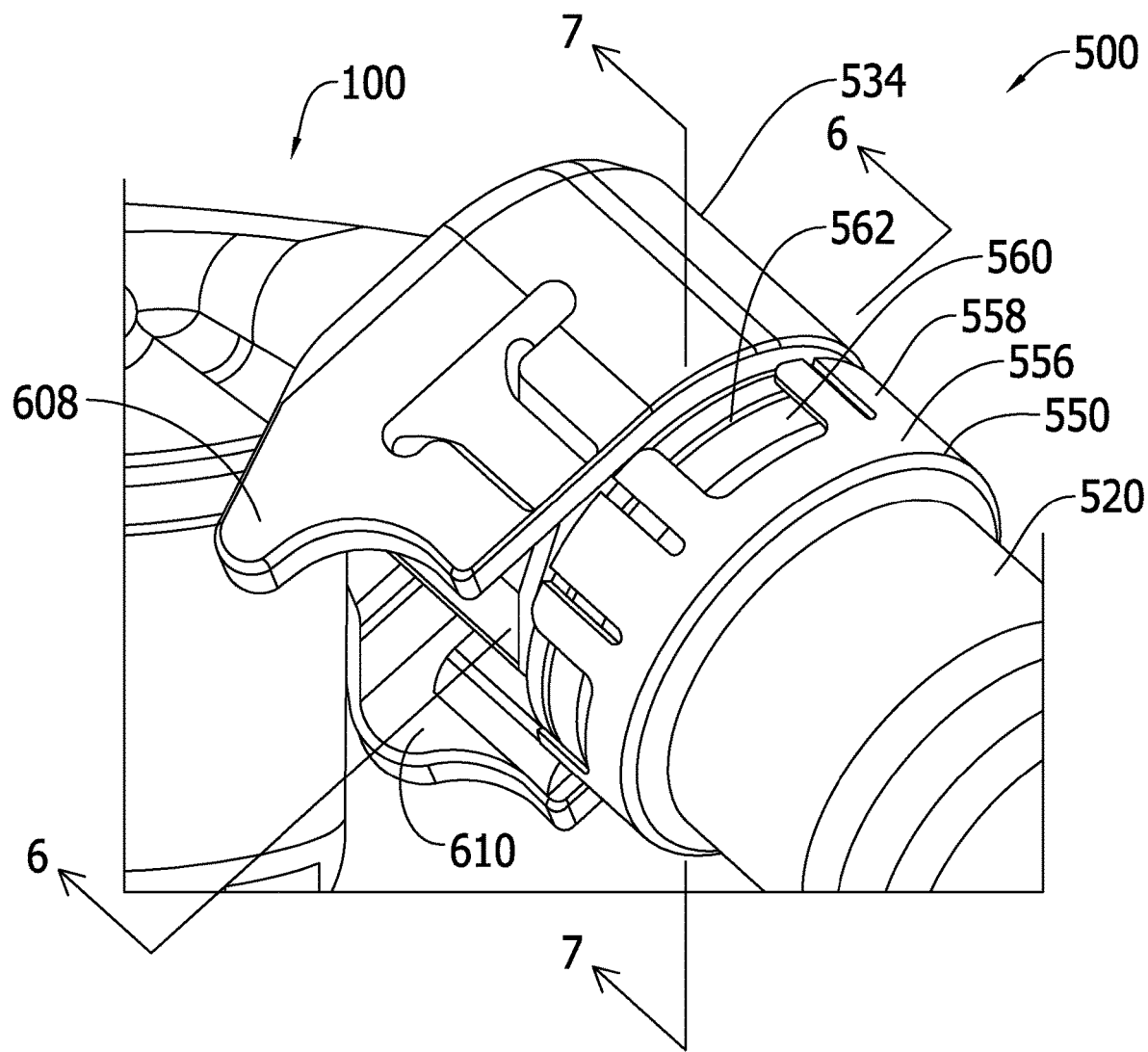
FIG. 5 is a perspective view of an outflow graft assembly.
Figure 6:
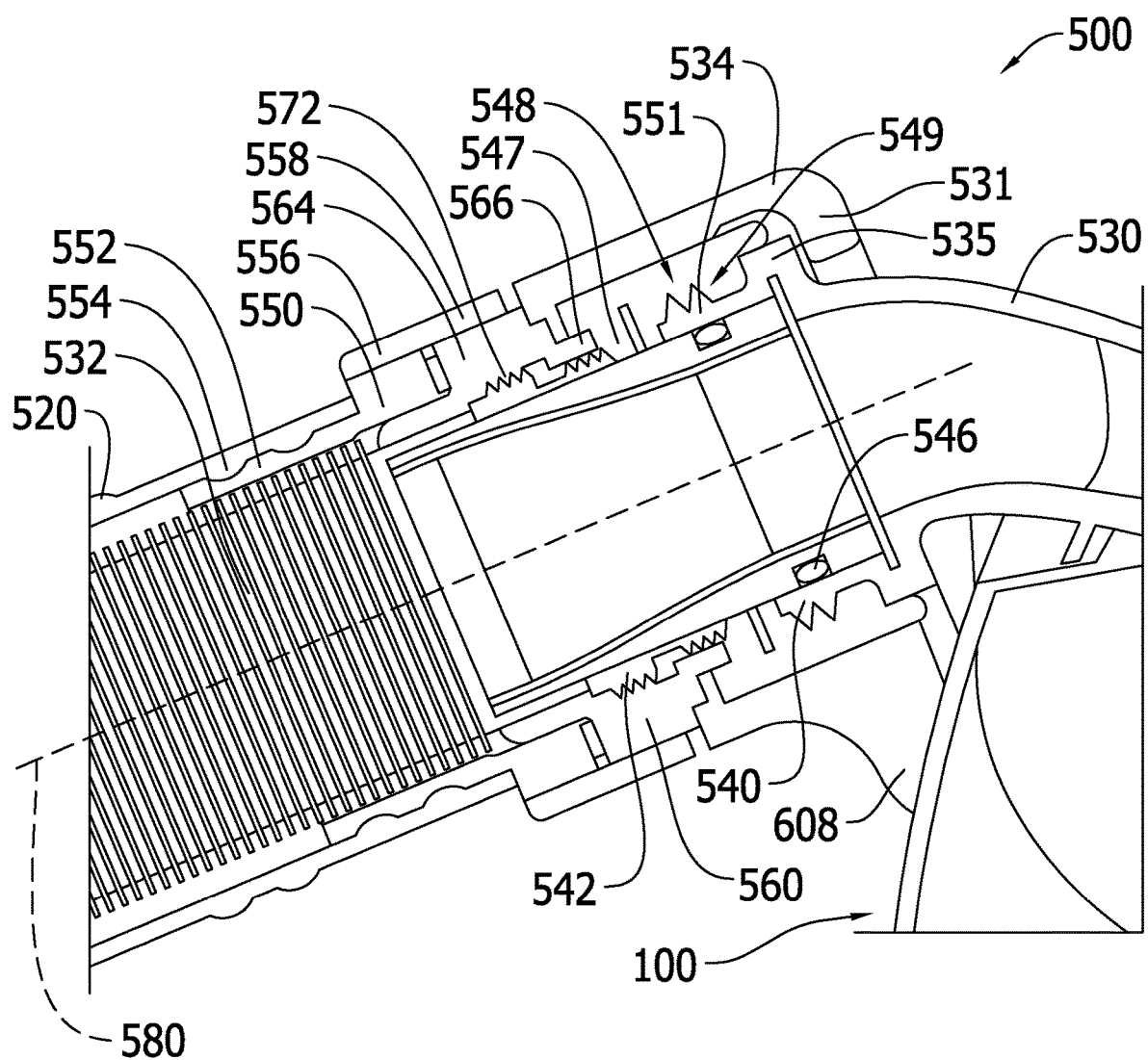
FIG. 6 is a cross-sectional view of the outflow graft assembly shown in FIG. 5 taken along line 6-6.
Figure 7:
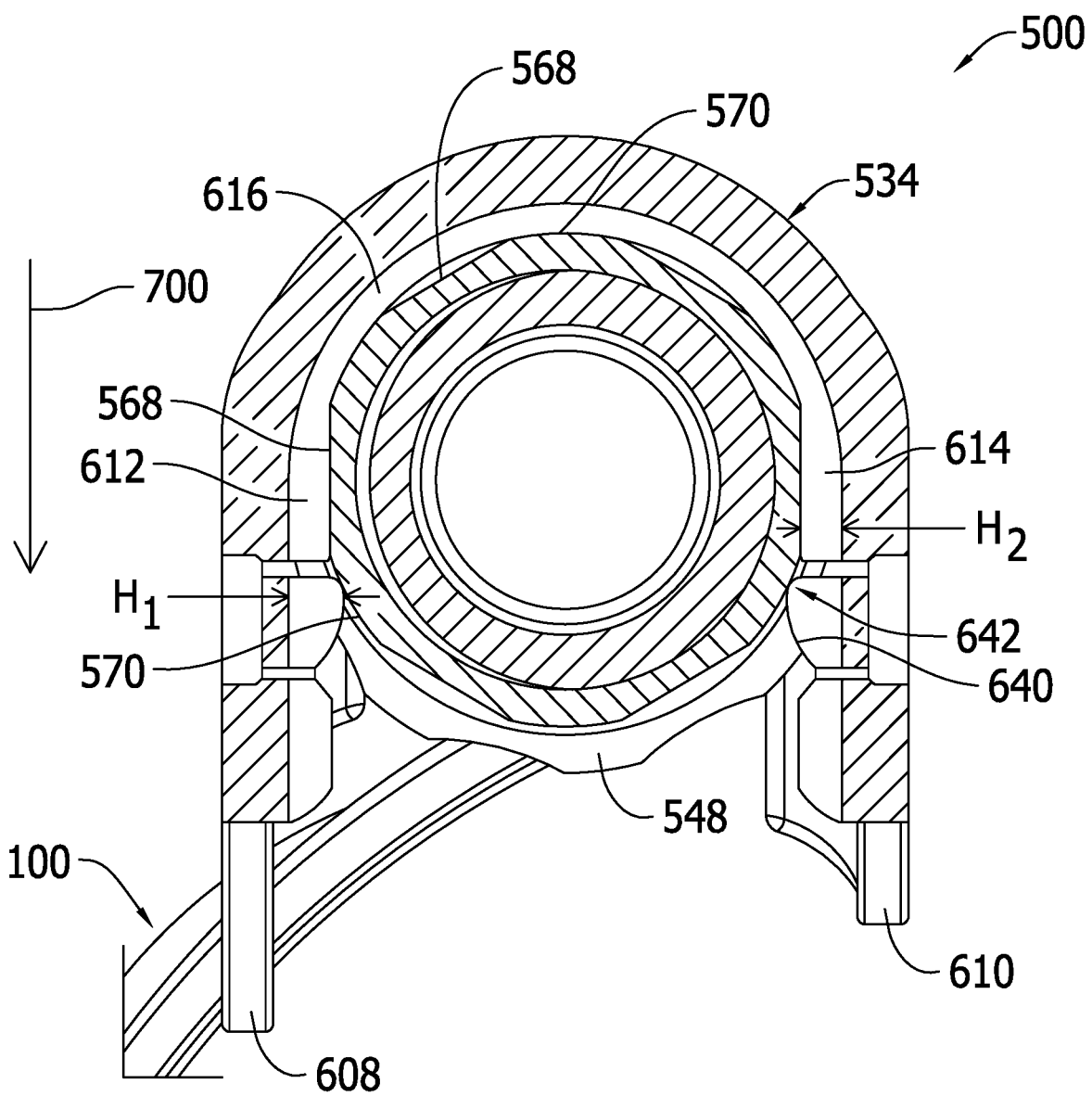
FIG. 7 is a cross-sectional view of the outflow graft assembly shown in FIG. 5 taken along line 7-7.

FIG. 5 is a perspective view of an outflow graft assembly 500. The outflow graft assembly 500 couples the blood pump assembly 100 to an outflow cannula (such as, for example, outflow cannula 20 (shown in FIG. 1)). FIG. 6 is a cross-sectional view of the outflow graft assembly 500 taken along line 6-6 (shown in FIG. 5), and FIG. 7 is a cross-sectional view of the outflow graft assembly 500 taken along line 7-7 (shown in FIG. 5).

More specifically, the outflow graft assembly 500 couples a pump cover 530 of the blood pump assembly 100 in flow communication with a graft 532 positioned in a bend relief 520 of the outflow cannula. The bend relief 520 forms an outer wall of the outflow cannula and allows for at least some flexibility/bending of the outflow cannula. The outflow graft assembly 500 includes a fixation clip 534 that prevents the graft 532 from rotating relative to the pump cover 530.

As shown in FIG. 6, in this embodiment, an outflow end 540 of the pump cover 530 receives a fluid transfer tube 542 that extends from the pump cover 530 to the graft 532. The fluid transfer tube 542 provides fluid communication between the pump cover 530 and the graft 532. The fluid transfer tube 542 includes a seal 546 (e.g., an o-ring) to prevent leakage of fluid flowing through the fluid transfer tube 542.

In this embodiment, the fluid transfer tube 542 is secured to the outflow end 540 of the pump cover 530 using a screw ring 548. Specifically, the screw ring 548 includes a first threaded surface 549 that engages a second threaded surface 551 on the outflow end 540. The screw ring 548 also includes an annular protrusion 547 that engages the fluid transfer tube 542 to secure an axial position of the fluid transfer tube 542 while allowing the fluid transfer tube 542 to rotate relative to the screw ring 548.

In some embodiments, the fixation clip 534 includes a lip 531 that engages a flange 535 of the pump cover 530. This engagement functions as an axial lock that prevents the screw ring 548 from disengaging from the outflow end 540. This may be particularly useful in embodiments where the fixation clip 524 is directly keyed to the screw ring 548 to prevent rotation of the screw ring 548, but may also be useful in embodiments where the fixation clip 524 is not directly keyed to the screw ring 548 (e.g., the embodiment shown in FIG. 7).

As shown in FIG. 6, the graft 532 is positioned within a bend relief clip 550 of the bend relief 520. The bend relief clip 550 includes a first segment 552 that is positioned between the graft 532 and a wall 554 of the bend relief 520. The bend relief clip 550 further includes a second segment 556 that is upstream from the first segment 552. In this embodiment, the second segment 556 has a larger diameter than the first segment 552. The bend relief clip 550 and bend relief 520 are able to freely rotate around the graft 532.

As best shown in FIGS. 5 and 6, the second segment 556 includes a plurality of axially extending fingers 558 that engage a graft nut 564 of a nut assembly 560. Specifically, the axially extending fingers 558 engage an annular groove 562 formed on the graft nut 564. The nut assembly 560 also includes a locking nut 566 having a generally hexagonal shape. Specifically, the locking nut 566 includes a plurality of planar edges 568 and corners 570, with one corner 570 extending between each pair of adjacent planar edges 568. At least a plurality of the planar edges 568 and corners 570 are positioned within the screw ring, and the planar edges 568 and corners 570 engage the fixation clip 534, as described herein. In this embodiment, the locking nut 566 is generally hexagonal, and includes six planar edges 568. Alternatively, the locking nut 566 may have suitable shape. For example, in some embodiments, the locking nut 566 has a generally octagonal shape (i.e., with eight planar edges 568).

As best shown in FIG. 6, the graft nut 564 including an interior surface 572 captures a metal ring sewn into the graft 532 to the fluid transfer tube 542 (while allowing rotation of the fluid transfer tube 542). The locking nut 566 then threads against the graft nut 564 to prevent the graft nut 564 from loosening. Accordingly, without the fixation clip 534 (described in detail below), rotation of the locking nut 566 about a longitudinal axis 580 of the outflow graft assembly 500 would result in corresponding rotation of the graft 532.

Accordingly, in this embodiment, the outflow graft assembly 500 includes the fixation clip 534 that inhibits rotation of the locking nut 566 (and accordingly inhibits rotation of the graft 532). That is, the fixation clip 534 keys the locking nut 566 and graft 532 to the pump cover 530.

Figure 8:
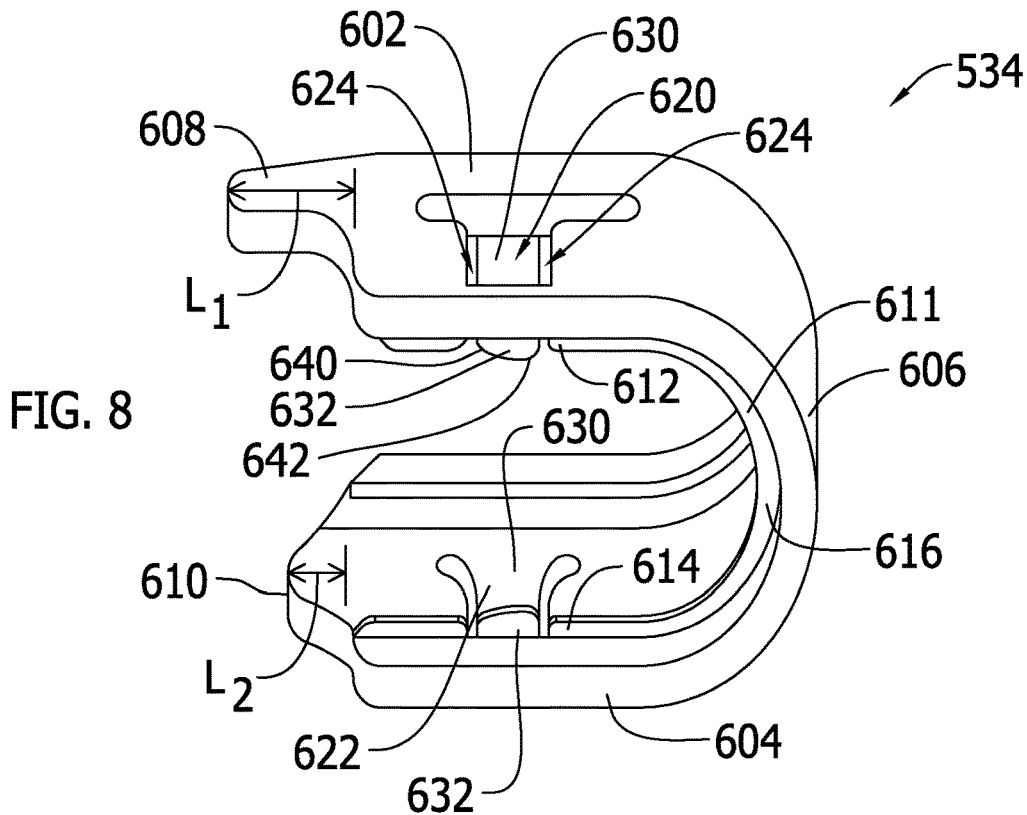
FIG. 8 is a perspective view of the fixation clip shown in FIG. 5.
Figure 9:
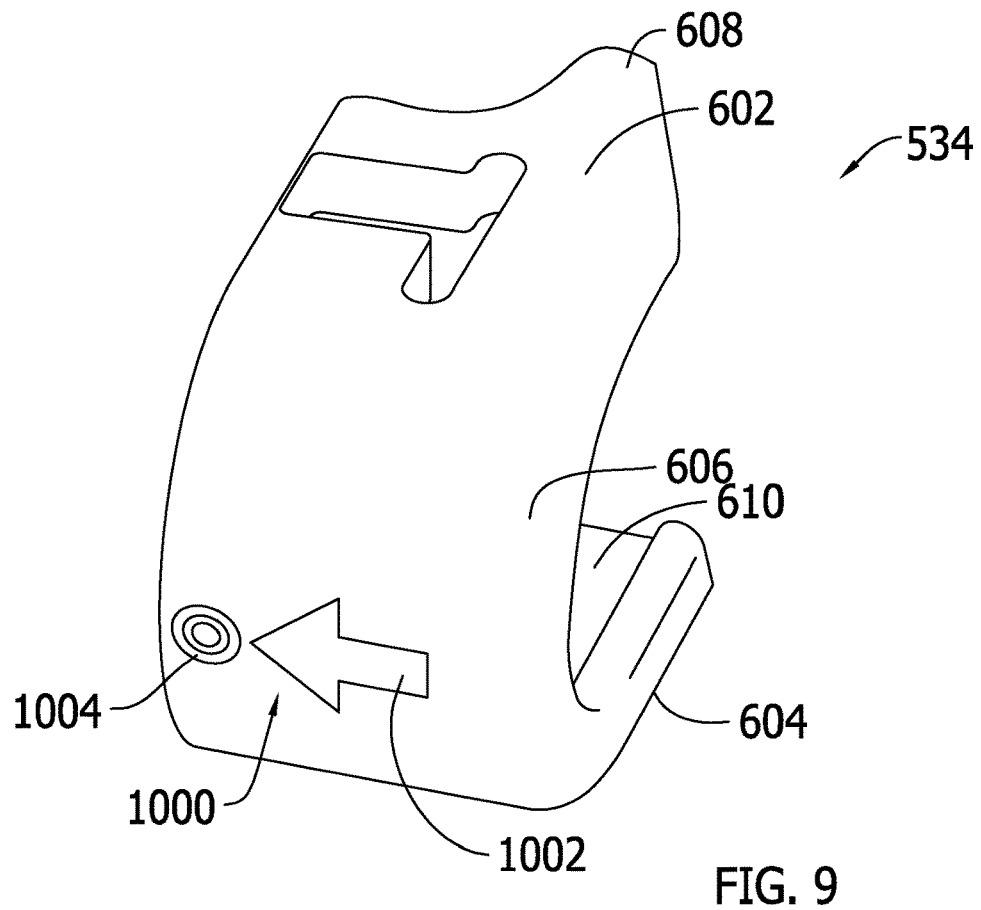
FIG. 9 is a perspective view of the fixation clip shown in FIG. 5.

FIGS. 8 and 9 are perspective views of the fixation clip 534. As shown in FIGS. 8 and 9, fixation clip 534 is generally U-shaped, and includes a first flat segment 602, a second flat segment 604, and an arcuate segment 606 extending between the first flat segment 602 and the second flat segment 604. A first foot 608 extends from the first flat segment 602, and a second foot 610 extends from the second flat segment 604.

As best shown in FIG. 8, a U-shaped lip 611 runs along a portion of the first flat segment 602, the arcuate segment 606, and a portion of the second flat segment 604. The lip 611 includes a first flat 612 on the first flat segment 602, a second flat 614 on the second flat segment 604, and an arc 616 extending between the first flat 612 and the second flat 614.

In this embodiment, the first flat segment 602 further includes a first flexure 620 and the second flat segment 604 includes a second flexure 622. Each of the first and second flexures 620 and 622 is defined by a pair of slits 624 in the first flat segment 602 and the second flat segment 604, respectively. Each of the first and second flexures 620 and 622 includes a body 630 and a locking feature 632. The locking feature 632 is located at a free end of the body 630 and extends inward from the body 630.

Because of the slits 624, and because the body 630 of each of the first and second flexures 620 is relatively thin, the first and second flexures 620 and 622 (and in particular, the locking features 632) are capable of flexing inward and outward relative to the rest of the first flat segment 602 and the second flat segment 604, respectively. Further, the first and second flexures 620 are sufficiently stiff such that if a force biases the first and second flexures 620 to flex outward from a resting position (i.e., the position shown in FIG. 8), the first and second flexures 620 will return to their resting position (by flexing inward) once the force is removed.

Each locking feature 632 has an engagement edge 640 including a peak 642. As shown best in FIG. 7, a height H1 of each locking feature 632 at the peak 642 is greater than a height H2 of the first flat 612 and the second flat 614. This enables the fixation clip 534 to prevent rotation of the locking nut 566, as described herein.

To prevent rotation of the locking nut 566, the fixation clip 534 is slid over the screw ring 548 and the locking nut 566 along an installation direction 700 (shown in FIG. 7). As the fixation clip 534 is slid over the locking nut 566, the locking features 632 each contact one of the planar edges 568 and flex outward. After passing over the planar edges 568, the locking features 632 flex back inward. When the locking features 632 flex back inward, the peak 642 of each locking feature 632 contacts an associated corner 570 (as best shown in FIG. 7). Further, the first flat 612 and the second flat 614 contact the planar edges 568 that the locking features 632 slid over.

The contact between the first and second flats 612 and 614 and the planar edges 568 prevents the locking nut 566 from rotating relative to the fixation clip 534, and the contact between the peaks 642 and the corners 570 prevents the fixation clip 534 from disengaging from the locking nut 566. Further, the fixation clip 534 slides over the screw ring 548 without engaging the screw ring 548, which reduces redundant keying risks. Accordingly, the fixation clip 534 prevents rotation of the graft 532.

As shown in FIG. 8, the first foot 608 extending from the first flat segment 602 has a first length L1, and the second foot 610 extending from the second flat segment 604 has a second length L2. As shown best in FIG. 5, when the fixation clip 534 is installed over the locking nut 566, the first foot 608 and the second foot 610 contact the peripheral wall 134 of the blood pump assembly 100. The difference in lengths between the first foot 608 and the second foot 610 ensures that the first foot 608 and the second foot 610 are complementary to the shape of the peripheral wall 134. The contact between the first foot 608, the second foot 610, and the peripheral wall 134 prevents the fixation clip from rotating relative to the peripheral wall 134, ensuring that the graft 532 does not rotate about the longitudinal axis 580.

In this embodiment, the fixation clip 534 is made of titanium. Alternatively, the fixation clip 534 may be made of any suitable material that enables the fixation clip 534 to function as described herein. Further, the fixation clip 534 is integrally formed as a single piece, and requires no tools to install or remove due to the arrangement of the first and second flexures 620 and 622. In addition, the fixation clip 534 can be installed on existing pump assemblies.

As shown in FIG. 9, the fixation clip 534 may include one or more markings 1000 that assist a user in installing the fixation clip 534. For example, in this embodiment, the markings 1000 include a first marking 1002 that indicates a flow direction and a second marking 1004 that indicates where the user should apply pressure when installing the fixation clip 534. Alternatively, the fixation clip 534 may include any suitable markings 1000.

Experimental testing verified that the fixation clip 534 prevents any substantial rotation of the locking nut 566. For example, in one study, the fixation clip was subjected to 2.6 million cycles of application of a 2.1 in-lbs. torque force. During that study, the average clockwise rotation was 1.8°, and the average counterclockwise rotation was 1.2°.

To remove the fixation clip 534, force may be applied to the first foot 608 and the second foot 610 in a direction opposite to the installation direction 700. Lateral forces applied in a direction perpendicular to the installation direction 700 and perpendicular to the longitudinal axis 580 only force the fixation clip 534 towards further installation or result in a torque being applied to the fixation clip 534. Further, axial forces applied along the longitudinal axis 580 are incapable of dislodging the fixation clip 534.

As described herein, the outflow graft assemblies of the present disclosure provide several advantages over previous VAD designs. For example, the fixation clip described herein prevents rotation of a locking nut coupled to a graft. This prevents rotation of the graft.

Although the embodiments and examples disclosed herein have been described with reference to particular embodiments, it is to be understood that these embodiments and examples are merely illustrative of the principles and applications of the present disclosure. It is therefore to be understood that numerous modifications can be made to the illustrative embodiments and examples and that other arrangements can be devised without departing from the spirit and scope of the present disclosure as defined by the claims. Thus, it is intended that the present application cover the modifications and variations of these embodiments and their equivalents.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An outflow graft assembly for an implantable blood pump, the outflow graft assembly comprising:
   a graft;
   a locking nut coupled to the graft, the locking nut comprising a plurality of planar edges and a plurality of corners, each corner extending between a pair of the plurality of planar edges; and
   a U-shaped fixation clip comprising:
      a first flat segment comprising a first flexure defined by a pair of slits formed in the first flat segment, the first flexure comprising a first locking feature;
      a second flat segment comprising a second flexure defined by a pair of slits formed in the second flat segment, the second flexure comprising a second locking feature;
      an arcuate segment extending between the first flat segment and the second flat segment; and
      a lip comprising a first flat on the first segment and a second flat on the second segment, wherein the U-shaped fixation clip is configured to engage the locking nut such that the first and second locking features contact associated corners of the plurality of corners and the first and second flats contact associated planar edges of the plurality of planar edges, thereby preventing rotation of the locking nut relative to the fixation clip.

2. The outflow graft assembly of claim 1, wherein the U-shaped fixation clip further comprises a first foot extending from the first flat segment and a second foot extending from the second flat segment.

3. The outflow graft assembly of claim 2, wherein the first foot has a first length, wherein the second foot has a second length, and wherein the first length is greater than the second length.

4. The outflow graft assembly of claim 2, wherein the first foot and the second foot are configured to contact a peripheral wall of a pump assembly to key the U-shaped fixation clip to the pump assembly when the U-shaped fixation clip engages the locking nut.

5. The outflow graft assembly of claim 1, further comprising:
   a pump cover;
   a fluid transfer tube providing fluid communication between the pump cover and the graft, the fluid transfer tube threadably coupled to the locking nut; and
   a screw ring threadably coupled to the pump cover.

6. The outflow graft assembly of claim 5, wherein the U-shaped fixation clip further comprises an engagement lip that engages a flange formed on the pump cover to prevent movement of the screw ring.

7. The outflow graft assembly of claim 5, wherein the U-shaped fixation clip is configured to slide over the screw ring without engaging the screw ring.

8. The outflow graft assembly of claim 1, wherein the first flexure is configured to flex inward and outward relative to the rest of the first flat segment.

9. The outflow graft assembly of claim 1, wherein the U-shaped fixation clip is integrally formed as a single piece of titanium.

10. The outflow graft assembly of claim 1, wherein each of the first and second locking features comprises an engagement edge including a peak.

11. The outflow graft assembly of claim 10, wherein a height of the first locking feature at the peak is greater than a height of the first flat.

12. A fixation clip for an outflow graft assembly of an implantable blood pump, the fixation clip comprising:

a first flat segment comprising a first flexure defined by a pair of slits formed in the first flat segment, the first flexure comprising a first locking feature;

a second flat segment comprising a second flexure defined by a pair of slits formed in the second flat segment, the second flexure comprising a second locking feature;

an arcuate segment extending between the first flat segment and the second flat segment; and a lip comprising a first flat on the first segment and a second flat on the second segment, wherein the fixation clip is configured to engage a locking nut such that the first and second locking features contact associated corners of a plurality of corners of the locking nut and the first and second flats contact associated planar edges of a plurality of planar edges of the locking nut, thereby preventing rotation of the locking nut relative to the fixation clip.

13. The fixation clip of claim 12, wherein the fixation clip further comprises a first foot extending from the first flat segment and a second foot extending from the second flat segment.

14. The fixation clip of claim 13, wherein the first foot has a first length, wherein the second foot has a second length, and wherein the first length is greater than the second length.

15. The fixation clip of claim 13, wherein the first foot and the second foot are configured to contact a peripheral wall of a pump assembly to key the fixation clip to the pump assembly when the fixation clip engages the locking nut.

16. The fixation clip of claim 12, wherein the first flexure is configured to flex inward and outward relative to the rest of the first flat segment.

17. The fixation clip of claim 12, wherein the fixation clip is integrally formed as a single piece.

18. The fixation clip of claim 12, wherein the fixation clip is titanium.

19. The fixation clip of claim 12, wherein each of the first and second locking features comprises an engagement edge including a peak.

20. The fixation clip of claim 19, wherein a height of the first locking feature at the peak is greater than a height of the first flat.

* * * * *